United States Patent [19]

Stone et al.

[11] Patent Number: 5,281,607

[45] Date of Patent: Jan. 25, 1994

[54] METHOD OF USING ALPHA 2-ANTAGONISTS FOR THE TREATMENT OF NEURODEGENERATIVE DISEASES

[75] Inventors: Eric A. Stone, Chappaqua; Guoying Bing, Forest Hills, both of N.Y.

[73] Assignee: New York University, New York, N.Y.

[21] Appl. No.: 957,551

[22] Filed: Oct. 8, 1992

[51] Int. Cl.$^5$ ............................................. A61K 31/44
[52] U.S. Cl. .................................... 514/280; 514/396; 514/401; 514/402
[58] Field of Search ................ 514/280, 396, 401, 402

[56] References Cited

U.S. PATENT DOCUMENTS 5,059,627  10/1991  Goto et al. ........................... 514/688
5,102,906  4/1992   Nakayama et al. .................. 514/452

FOREIGN PATENT DOCUMENTS 0335637  10/1989  European Pat. Off.
2491926  10/1980  France ....................... A61K 31/47
9102067   2/1992  World Int. Prop. O.

OTHER PUBLICATIONS

Fabrazzo, E. et al., "Stimulation of Nerve Growth Factor Biosynthesis in Developing Rat Brain by Reserpine: Steriods as Potential mediators, Molecular Pharmacology," *Molecular Pharmacology*, 39:144–149 (1990).

Schwartz, Joan P., "Stimulation of Nerve Growth Factor mRNA Content in C6 Glioma Cells by a β-Adrenergic Receptor and by Cyclic AMP," *GLIA*, 1:282–285 (1988).

Furukawa, Y et al., "Catecholamines increase nerve growth factor mRNA content in both mouse astroglial cells and fibroblast cells," *FEBS Letters*, vol. 247, No. 2:463–467 (1987).

Dal Toso, R. et al., "Beta Adrenergic and Prostaglandin Receptor Activation increases Nerve Growth Factor mRNA Content in C6-2B Rat Astrocytome Cells," *The Journal Pharmacology and Experiment Therapeutics*, 246(3):1190–1193 (1988).

Mocchetti, I. et al., "Regulation of nerve growth factor biosynthesis by β-adrenergic receptor activation in astrocytoma cells: A potential role of c-Fos protein," *Proc. Natl. Acad. Sci. USA*, 86:3891–3895(1989).

Furukawa, Y. et al., "Catecholamines Induce an Increase in Nerve Growth Factor Content in the Medium of Mouse L-M Cells," *The Journal of Biological Chemistry*, vol. 261(13):6039–6047 (1986).

Dal Toso, R. et al., "Beta-Adrenergic Receptor Regulation of NGF-nRNA Content in Rat C6-2B Glioma Cells," *Neuropharmacology*, vol. 26(12):1786(1987).

Onrot et al., *Medline Database*, AN87116310, Feb. 1987.

Nishino et al., *Chemical Abstracts*, 113(9):71217p, 1990.

*Primary Examiner*—S. J. Friedman
*Assistant Examiner*—William Jarvis
*Attorney, Agent, or Firm*—Browdy and Neimark

[57] ABSTRACT

The treatment of neurodegenerative diseases by the stimulation of endogenous or recombinant expression in vivo of nerve growth factor in the central nervous system by administration of a therapeutically effective amount of an $\alpha_2$-antagonist.

4 Claims, 1 Drawing Sheet

METHOD OF USING ALPHA 2-ANTAGONISTS FOR THE TREATMENT OF NEURODEGENERATIVE DISEASES

This invention was made with government support under NIMH grant #: MH45265 awarded by the National Institute of Mental Health. The government has certain rights in the invention.

BACKGROUND OF THE INVENTION

Field of the Invention

The present invention relates to the treatment of neurodegenerative diseases and/or central nervous system trauma by the stimulation of endogenous or recombinant expression in vivo of nerve growth factor in the central nervous system.

Description of the Background Art

Nerve growth factor (NGF) is a neurotrophic agent which is necessary for the development and maintenance of peripheral sympathetic and sensory neurons and of central cholinergic neurons. The control of NGF production in the brain is not presently understood.

Recent findings have suggested that NGF may be useful as a therapeutic tool for treating neurodegenerative diseases which are characterized by defective neuronal plasticity (Levi-Montalcini 237:1154,1162 (1987); Hefti et al. *Ann. Neurol.* 20:275.281 (1986)). However, NGF cannot be administered parenterally due to the presence of the blood brain barrier, and so pharmacological agents that enhance brain NGF biosynthesis might represent an appropriate alternative to parenteral administration of NGF as a brain therapeutic agent.

However, the establishment of in vivo efficacy of a potential brain NGF stimulating therapeutic agent is not predictable, based on in vitro data, due to several criteria required to show in vivo efficacy, and in vivo administration of an NGF stimulating therapeutic agent must be shown to pass the blood brain barrier, have specific binding to appropriate receptors with specificity and selectivity, as well as showing of stimulation of NGF production, such as NGF transcription, in order for in vivo efficacy to be established.

In particular, it has been determined in the art of brain pharmaceuticals, including therapeutic and imaging agents, that at least three criteria, as listed below, must be met in order for a putative brain therapeutic or imaging agent to be found suitable for in vivo brain therapeutic or imaging treatment. These criteria include, but are not limited to, the following. One criteria is that such agents must pass the blood brain barrier by meeting a lower and upper lipophilic threshold, wherein a neuropharmaceutical must be lipophilic enough to penetrate the blood-brain barrier. Lipid insoluble molecules, with very few exceptions, do not penetrate into the brain. Similarly, the compound cannot be too lipophilic; if it is, it will bind non-specifically to cell membranes, resulting in generalized distribution in the brain, mimicking the action of a blood flow agent as opposed to a specific receptor imaging agent.

Another criteria is metabolic stability of the brain therapeutic or imaging agent after administration. The agent must be sufficiently metabolically stable in the brain to allow for its therapeutic or imaging effects by binding to the appropriate receptor. A third criteria is the retention of receptor specificity and selectivity of the brain therapeutic or imaging agent for the particular receptor for which it is specific, while at the same time having a high selectivity by having a low binding to other, non-target receptors. For example, the agent must retain its specificity and selectivity at 37° C., which is not always true for compounds tested in vitro, where incubation conditions are typically 4° C. or at ambient room temperature. It is well-known that affinity and metabolic rate are greatly influenced by temperature. These criteria are presented in the following references: Arendt, R.M. et al., *Cardiology* 71:307.314 (1984); Garvey, H.L. et al., *J. Pharmacol. Exp. Ther.* 194:220–233 (1975); Arnett, C.D. et al., *J. Neurochem.* 44:835 (1985); Arnett, C.D. et al., *J. Nucl. Med.* 27:1878.1882 (1986); Kung, H.F., *Nuc. Med. Biol.* 17:85.92 (1990).

Unless, at a minimum, the above three criteria are met, then the putative brain therapeutic agent is not predictably shown to be suitable for in vivo brain therapy, as showing a correlation with in vivo efficacy. For example, if a agent passes the blood brain barrier and binds receptors, but does not have metabolic stability or loses its selectivity or specificity, then such a agent is not suitable for in vivo brain therapy.

Moccheti et al, *Proc. Nat'l Acad. Sci. USA*, 86:3891-5 (May, 1989); Schwartz, GLIA, 1:282.5 (1988); Dal Toso et al, *J. Pharmacol. Exp. Ther.*, 246:1190-3 (Sept. 1988); Dal Toso et al, *Neuropharmacology* 26:1783 - 6 (Dec. 1987); and Schwartz and Mishler, *Cellular and Molecular Neurobiology* 10:447–457 (1990), disclose that isoproterenol stimulation of beta-adrenergic receptors, in vitro, increases nerve growth factor biosynthesis in C6 rat glioma cells. However, Siminoski et al., *Endocrinology* 121:1432–1437 (1987), found that 17β-estradiol reduces NGF levels in vitro. However, as presented above, such in vitro findings do not predictably suggest that such stimulation will occur by isoproterenol in vivo.

Schwartz and Mishler, supra, disclose that isoproterenol stimulates NGF mRNA content, in vitro, in cortical astrocytes, which is blocked by the noradrenergic antagonist propranolol, but not by the alpha-antagonist phenoxybenzamine, such that CNS astrocytes may serve as a source of NGF in that the NGF gene is one of a class of separate cAMP regulated genes.

With regard to what has been found in vivo, Fabrazzo et al., *Molecular Pharmacology* 39:144–149 (1991), found that rats having depleted catecholamine, due to reserpine treatment, were found to be associated with a three fold increase in NGF mRNA in the cerebral cortex, such that NGF biosynthesis in the central nervous system might be inhibited by adrenocortical hormonal secretion.

Accordingly, Fabrazzo suggests that induction of the release of catecholamines, such as norepinephrine, does not have the effect of increasing NGF mRNA. Fabrazzo et al states, in the discussion at page 148, that "reserpine, through the initial release of catecholamine, could increase NGF mRNA by increasing noradrenaline receptor occupancy. This possibility was ruled out because a pretreatment with 1-propranolol, a BAR (beta-adrenergic receptor) blocker, or with yohimbine, an $\alpha_2$-adrenergic receptor blocker, failed to antagonize the effect of reserpine on NGF biosynthesis." Accordingly, Fabrazzo teaches away from the use of chatecholamine stimulation of NGF mRNA, including the use of beta adrenergic receptor stimulation.

U.S. Pat. No. 5,059,627, assigned to Takeda Chemical, discloses a NGF secretion factor inducer as 1,4 benzoquinone compounds.

Japanese laid open patent No. JP 2067223 discloses a cerebral hyperergic drug which promotes NGF protein in the brain.

EP 335 637 discloses NGF receptor peptides capable of inducing an NGF-associated biological response in rat root ganglia, as an NGF agonist or antagonist.

U.S. Pat. Nos. 4,985,458 and 5,102,906 disclose catechol derivatives that are useful for inducing production and secretion of NGF in treating regressive disorders of the central nervous system.

PCT publication No. WO91/02067 (February 21, 1991), discloses regulation of CNS NGF levels using cytokines, which can be used to treat neurologic disorders such as Ahlzeimers' disease.

Accordingly, while the art teaches away from the induction of NGF by endogenous catecholamine or adrenergic receptor in vivo induction in the central nervous system, as exemplified by Fabrazzo et al., there is a need to provide compounds or compositions that induce NGF biosynthesis in the brain for treatment of neurodegenerative diseases and/or trauma to the central nervous system, since parenteral administration of NGF does not result in entry of the administered NGF into the brain.

Citation of the above documents is not intended as an admission that an of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It is an object of the present invention to overcome one or more of the deficiencies of the related art.

It is another object of the present invention to provide methods for the treatment of neurodegenerative diseases by stimulation of endogenous or recombinant expression, in vivo, of nerve growth factor in the central nervous system through the administration of a therapeutically effective amount of at least one of a $\beta$-adrenergic agonist, an $\alpha_1$-adrenergic agonist, and/or an $\alpha_2$-adrenergic antagonist, wherein $\alpha$-adrenergic antagonists are preferred.

Other objects of the invention will be apparent to skilled practitioners from the following detailed description and examples relating to the present invention.

DETAILED DESCRIPTION OF THE PREFERRED EMBODIMENTS

Figure 1:
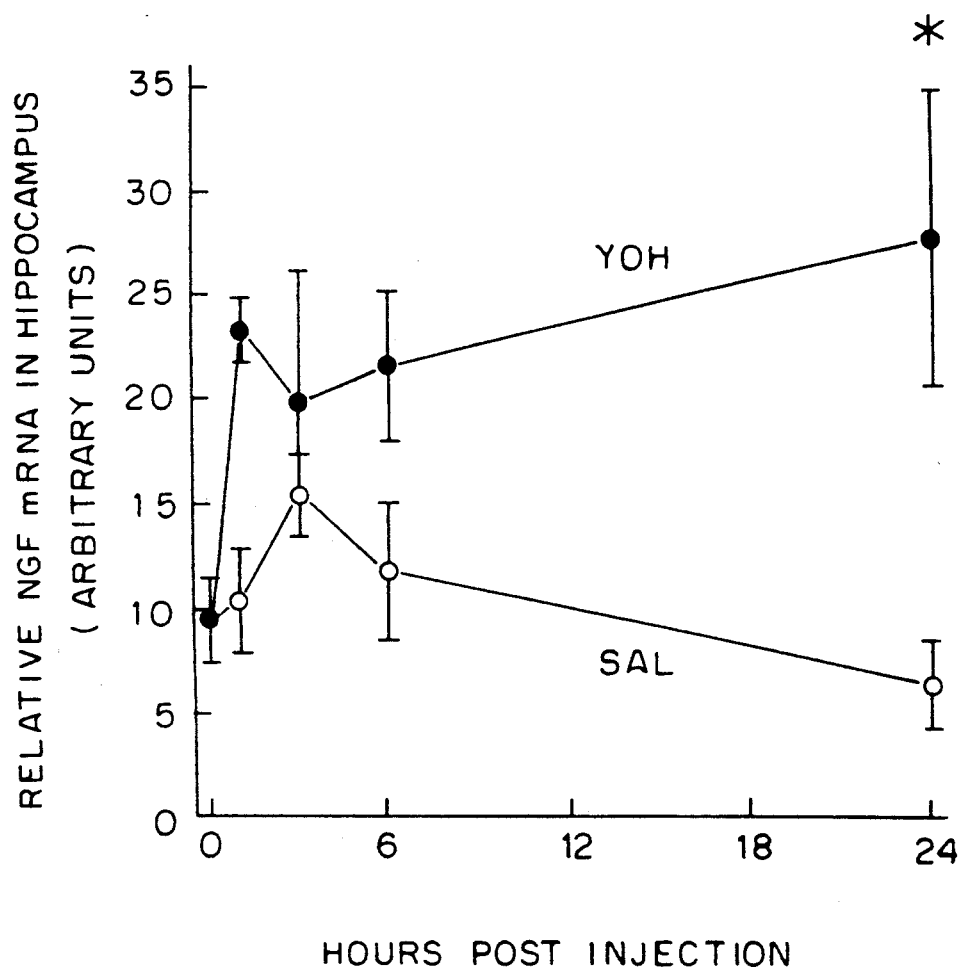
FIG. 1 is a graphical representation of the effect of injection of yohimbine (5.0 mg/kg, i.p.) (solid circles 8) or saline (empty circle) on levels of nerve growth factor mRNA in rat hippocampus, wherein each value represents the mean and SEM of 4–6 rats. The graph shows a significant difference between yohimbine and saline groups found at 24 hours ($p<0.05$).

The present invention relates to the treatment of neurodegenerative diseases and/or central nervous system trauma by the stimulation of endogenous or recombinant expression in vivo of nerve growth factor in the central nervous system through administration of an NGF central nervous system stimulating effective amount of at least one of a $\beta$-agonist, an $\alpha_1$-agonist, and/or an $\alpha_2$-antagonist.

Accordingly, the present invention provides, in one aspect, for the treatment of neurodegenerative diseases and/or trauma to the central nervous system by in vivo induction of NGF production in the central nervous system using at least one of a $\beta$-adrenergic agonist, an $\alpha$-adrenergic agonist, and a $\alpha_2$-adrenergic antagonist.

It has been discovered that the in vivo induction of NGF in the central nervous system is induced by at least one of an $\alpha_1$-agonist, an $\alpha_2$-antagonist or a $\beta$-agonist by stimulation of epinephrine production in neurotransmission.

Accordingly, the use of at least one $\alpha_1$-agonist, an $\alpha_2$-antagonist or a $\beta$-agonist can be used to stimulate NGF production in the central nervous system since such compounds pass the blood brain barrier, specifically bind $\alpha_1$ and $\beta$ receptors, and are biologically active in stimulating the production of NGF in the central nervous system which has a therapeutic effect on neurodegenerative and/or neurotraumatic pathologies.

Non-limiting examples of $\beta$-adrenergic agonists include dobutamine, prenalterol, clenbuterol, isoproterenol, epinephrine, fenoterol, albuterol, terbutaline, metaproterenol, salbutamol, zinterol, rimiterol and tazolol. Non-limiting examples of $\alpha_1$-adrenergic agonists include phenylephrine, methoxamine, St.587, circazoline, modafinil and analogues thereof. Non-limiting examples of $\alpha_2$-adrenergic antagonists include yohimbine, tolazoline, idazoxan, rauwolscine, atipamizole and related compounds.

According to the present invention, neurodegenerative diseases can be treated by administration of compounds which pass the blood brain barrier and act on the central nervous system to induce nerve growth factor production.

Neurodegenerative pathologies which can be treated according to a method of the present invention include, but are not limited to the following:

demyelinating diseases, such as multiple sclerosis and acute transverse myelitis;

extrapyramidal and cerebellar disorders, such as lesions of the corticospinal system;

disorders of the basal ganglia or cerebellar disorders;

hyperkinetic movement disorders such as 15 Huntington's Chorea and senile chorea;

drug-induced movement disorders, such as those induced by drugs which block CNS dopamine receptors;

hypokinetic movement disorders, such as Parkinson's disease;

progressive supra-nucleo palsy;

structural lesions of the cerebellum;

spinocerebellar degenerations, such as spinal ataxia, Friedreich's ataxia, cerebellar cortical degenerations, multiple systems degenerations (Mencel, Dejerine-Thomas sporadic or recessive disorder, Shi-Drager, and Machado-Joseph disease);

systemic disorders (Refsum's disease, abetalipoproteinmia, ataxia telangiectasia, and mitochondrial multi-system disorder);

disorders of the motor unit, such as neurogenic muscular atrophies (anterior horn cell degeneration, such as amyotrophic lateral sclerosis (ALS), infantile spinal muscular atrophy and juvenile spinal muscular atrophy);

Alzheimer's disease;

Down's Syndrome in middle age;

Diffuse Lewy body disease;
Senile Dementia of Lewy body type;
Wernicke-Korsakoff syndrome;
the effects of chronic alcoholism;
Creutzfeldt-Jakob disease;
Subacute sclerosing panencephalitis
Hallerrorden-Spatz disease;
Dementia pugilistica;

neurological developmental diseases, such as those due to premature delivery or cocaine addiction. Additionally, trauma of the central nervous system can similarly be treated by a method according to the present invention. Non-limiting examples are trauma of the central nervous system, including head injury, postconcussion syndrome and spinal cord injury. See, e.g., Berkow et al, eds., The Merck Manual, 15th edition, Merck and Co., Rahway, N.J., 1987; Goodman et al., eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, MD. (1987), Katzung, ed. Basic and Clinical Pharmacology, Fifth Edition, Appleton and Lange, Norwalk, Conn. (1992), which references and references cited therein, are entirely incorporated herein by reference for preparation and administration of pharmaceutical companies.

Pharmaceutical Preparations for Use in Methods of the Present Invention

A preparation of at least one $\beta$-agonist, $\alpha_1$-agonist, and/or $\alpha_2$-antagonist for parenteral administration includes sterile aqueous or non-aqueous solutions, suspensions, and emulsions, which may contain auxiliary agents or excipients which are known in the art.

Pharmaceutical compositions such as tablets and capsules can also be prepared according to known method steps.

By the term "protection" from infection or disease as used herein is intended "prevention," "suppression" or "treatment." "Prevention" involves administration of at least one $\beta$-agonist, $\alpha_1$-agonist, and/or $\alpha_2$-antagonist prior to the induction of the disease.

"Suppression" involves administration of at least one $\beta$-agonist, $\alpha_1$-agonist, and/or $\alpha_2$-antagonist during the induction of the disease.

"Treatment" involves administration of at least one $\beta$-agonist, $\alpha_1$-agonist, and/or $\alpha_2$-antagonist after the appearance of the disease. It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

At least one $\beta$-agonist, $\alpha_1$-agonist, and/or $\alpha_2$-antagonist, to be used in a method of the present invention, may be administered by any means that achieve their intended purpose, for example, to treat neurodegenerative or neurotraumatic related pathologies, using at least one $\beta$-agonist, $\alpha_1$-agonist, and/or $\alpha_2$-antagonist, in the form of a pharmaceutical composition.

For example, administration of such a composition may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

A preferred mode of using a pharmaceutical composition containing at least one $\beta$-agonist, $\alpha_1$-agonist, and/or $\alpha_2$-antagonist in a method of the present invention is by oral administration or intravenous application.

A typical regimen for preventing, suppressing, or treating neurodegenerative or neurotraumatic related pathologies, such as, but not limited to, such pathologies described herein, comprises administration of an effective amount of at least one $\beta$agonist, $\alpha_1$-agonist, and/or $\alpha_2$-antagonist administered over a period of one or several days, up to and including between one week and about 24 months.

It is understood that the dosage of at least one $\beta$agonist, $\alpha_1$-agonist, and/or $\alpha_2$-antagonist to be used in a method of the present invention, administered in vivo or in vitro, will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow, supra, Goodman, supra, Avery, supra and Katzung, supra, which are entirely incorporated herein by reference, including all references cited therein.

The total dose required for each treatment may be administered by multiple doses or in a single dose. At least one $\beta$-agonist, $\alpha_1$-agonist, and/or $\alpha_2$-antagonist may be administered alone or in conjunction with other therapeutics directed to neurodegenerative and/or CNS trauma related pathologies, as described herein.

Effective amounts of at least one $\beta$agonist, $\alpha_1$-agonist, and/or $\alpha_2$-antagonist containing composition, which may also include other compounds or compositions that are known to be useful in treating pathologies involving neurodegenerative diseases and/or CNS trauma, are from about 0.01 mg to about 100 mg/kg body weight, and preferably from about 10 mg to about 50 mg/kg body weight, such 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg.

Preparations for parenteral administration include sterile aqueous or non aqueous solutions, suspensions, and emulsions, which may contain auxiliary agents or excipients which are known in the art. Pharmaceutical compositions such as tablets and capsules can also be prepared according to routine methods. See, e.g., Parrott, Pharmaceutical Technology, Burgess Publishing Co., Minneapolis, Minn., (1970); Barker, supra, Goodman, supra, Avery, supra and Katzung, supra, which are entirely incorporated herein by reference, including all references cited therein.

Pharmaceutical compositions comprising at least one $\beta$-agonist, $\alpha_1$-agonist, and/or $\alpha_2$-antagonist such as 1-10 or 1, 2, 3, 4, 5, 6, 7, 8, 9 or 10 $\beta$- and $\alpha_1$-agonists and $\alpha_2$-antagonists, used in a method of the present invention, may include all compositions wherein at least one $\beta$-agonist, $\alpha_1$-agonist, and/or $\alpha_2$-antagonist is contained in an amount effective to achieve its intended purpose.

In addition to at least one β-agonist, $α_1$-agonist, and/or $α_2$-antagonist, a pharmaceutical composition may contain suitable pharmaceutically acceptable carriers, such as excipients, carriers and/or auxiliaries which facilitate processing of the active compounds into preparations which can be used pharmaceutically.

Pharmaceutical compositions comprising at least one β-agonist, $α_1$-agonist, and/or $α_2$-antagonist may also include suitable solutions for administration intravenously, subcutaneously, dermally, orally, mucosally, rectally or may by injection or orally, and contain from about 0.01 to 99 percent, preferably from about 20 to 75 percent of active component (i.e. the antibody) together with the excipient. Pharmaceutical compositions for oral administration include tablets and capsules. Compositions which can be administered rectally include suppositories. See, e.g., Parrott, supra, Berkow, supra, Goodman, supra, Avery, supra and Katzung, supra, which are entirely incorporated herein by reference, including all references cited therein.

Having now generally described the invention, the same will be more readily understood through reference to the following example which is provided by way of illustration, and is not intended to be limiting of the present invention.

EXAMPLE 1: IN VIVO CENTRAL NERVOUS SYSTEM STIMULATION OF NGF SYNTHESIS BY AN ALPHA-ANTAGONIST ACCORDING TO A METHOD OF THE PRESENT INVENTION.

Rats were either not injected or injected with either saline or yohimbine (5.0 mg/kg, i.p.) and sacrificed at varying intervals after injection. The brain was removed and the hippocampus dissected and frozen. Total RNA was prepared by the guanidinium thiocyanate-cesium chloride method. Nerve growth factor (NGF) mRNA was assayed by an RNase protection assay using a commercial kit (Ambion). The RNase assay provides the high sensitivity needed to detect nerve growth factor mRNA which is a low abundance message. It was found that yohimbine injection, compared to saline control, produced a significant increase in NGF mRNA levels (ANOVA, $p<0.05$). Neuman-Kuels comparisons revealed significant increases at the 24 hr post-injection intervals ($p<0.05$). It is concluded that yohimbine produces a significant increase in NGF mRNA in the rat hippocampus, in vivo, which is expected to highly correlate with clinical in vivo efficacy.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for treating an animal suffering from a neurodegenerative disease comprising parenterally or orally administering to said animal a nerve growth factor stimulating effective amount of at least one $α_2$-adrenergic receptor antagonist.

2. A method according to claim 1, wherein said at least one adrenergic receptor $α_2$-antagonist is selected from the group consisting of yohimbine, tolazoline, idazoxa, rauwolscine, atipamizole and analogs thereof.

3. A method according to claim 1, herein said animal is human.

4. A method according to claim 1, wherein said neurodegenerative disease is selected from the group consisting of a demyelinating disease; a drug-induced movement disorder; a hypokinetic movement disorder; a disorder of the motor unit; Alzheimer's disease; Down's Syndrome in middle age; Senile Dementia of Lewy body type; an effect of chronic alcoholism; Subacute sclerosing panencephalitis; a neurological developmental disease; infantile spinal muscular atrophy; and juvenile spinal muscular atrophy.

* * * * *

REEXAMINATION CERTIFICATE (3515th)
United States Patent [19]
Stone et al.

[11] B1 5,281,607
[45] Certificate Issued May 19, 1998

[54] METHOD OF USING α 2-ANTAGONISTS FOR THE TREATMENT OF NEURODEGENERATIVE DISEASES

[75] Inventors: Eric A. Stone, Chappaqua; Guoying Bing, Forest Hills, both of N.Y.

[73] Assignee: New York University, New York, N.Y.

Reexamination Request:
No. 90/004,557, Feb. 21, 1997

Reexamination Certificate for:
Patent No.: 5,281,607
Issued: Jan. 25, 1994
Appl. No.: 957,551
Filed: Oct. 8, 1992

[51] Int. Cl.$^6$ ................................................ A61K 31/44
[52] U.S. Cl. ..................... 514/280; 514/396; 514/401; 514/402; 514/280
[58] Field of Search ...................... 514/280, 396, 514/401, 402

[56] References Cited

PUBLICATIONS

Colpaert, "Pharmacological Characteristics of Tremor, Rigidity and Hypokinesia Induced by Reserpine in Rat," *Neuropharmacol.*, 26(9):1431–1440 (1987).

Chapleo, "The Discovery and Therapeutic Potential of Selective $\alpha_2$-Adrenoceptor Antagonists," *Recent Advances in Receptor Chemistry*, 85–106 (1988).

J. Ghika, "Idazoxan Treatment in Progress Supranuclear Palsy," *Neurology*, 41:986–991 (1991).

Goldberg et al, "Yohimbine: A Pharmacological Probe for Study of the Alpha–2–Adrenoreceptor," *Pharmacological Reviews*, 35(2):143–179 (1983).

Bing et al, "Noradrenergic activation of immediate early genes in rat cerebral cortex," *Molecular Brain Research*, 11:43–46 (Aug. 1991).

Colpaert et al, "Effects of an Alpha$_2$ Antagonist in a 20–Year–Old Java Monkey With MPTP–Induced Parkinsonian Signs," *Brain Research Bulletin*, 26:627–631 (Apr. 1991).

Sara, "Noradrenergic Modulation of Selective Attention: Its Role in Memory Retrieval," *Annals New York Academy of Sciences*, 444:178–193 (1985).

Sara et al, "Idazoxan, an α–2 Antagonist, Facilitates Memory Retrieval in the Rat," *Behavioral and Neural Biology*, 51(3):401–411 (1989).

Hefti et al, "Neurotrophic Factors and Parkinson's Disease," *Advances in Neurology, vol. 53:Parkinson's Disease: Anatomy, Pathology and Therapy* (Streifler et al, editor, New York, pp. 123–127 (1990).

Mavridis et al, "$\alpha_1$ and $\alpha_2$ antagonists differentially modulate D–amphetamine and apomorphine induced rotation in substantia nigra lesioned rats," *European Journal of Pharmacology*, 183(2):448 (Jul. 1990).

Altar, "Nerve Growth Factor and the Neostriatum," *Prog. Neuro–Psychopharmacol. & Biol. Psychiat.*, 15:157–169 (1991).

*Primary Examiner*—William R. A. Jarvis

[57] ABSTRACT

The treatment of neurodegenerative diseases by the stimulation of endogeneous or recombinant expression in vivo or nerve growth factor in the central nervous system by administration of a therapeutically effective amount of an $\alpha_2$-antagonist.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Amend the paragraph appearing at column 4, lines 45–46, as follows:
hyperkinetic movement disorders such as [15] Huntington's Chorea and senile chorea;

Amend the paragraph appearing at column 4, line 52, as follows:
progressive *supranuclear* [supra-nucleo] palsy;

Amend the paragraph appearing at column 6, lines 35–40, to read as follows:
The total dose required for each treatment may [5] be administered by multiple doses or in a single dose. At least one β-agonist, $\alpha_1$-agonist, and/or $\alpha_2$-antagonist may be administered alone or in conjunction with other therapeutics directed to neurodegenerative and/or CNS trauma related pathologies, as described herein.

2. A method according to claim [1] *5*, wherein said at least one adrenergic receptor $\alpha_2$-antagonist is selected from the group consisting of yohimbine, tolazoline, [idazoxa,] *idazoxan*, rauwolscine, atipamizole and analogs thereof.

3. A method according to claim [1] *5*, wherein said animal is human.

AS A RESULT OF REEXAMINATION, IT HAS BEEN DETERMINED THAT:

Claims 1 and 4 are cancelled.

Claim 2 and 3 are determined to be patentable as amended.

New claims 5 and 6 are added and determined to be patentable.

*5. A method for treating a neurodegenerative disease in an animal suffering from a neurodegenerative disease other than a hypokinetic movement disorder, progressive supranuclear palsy, or Alzheimer's disease, comprising parenterally or orally administering to said animal a nerve growth factor stimulating effective amount of at least one* $\alpha_2$*-adrenergic receptor antagonist.*

*6. A method according to claim 5, wherein said neurodegenerative disease is selected from the group consisting of a demyelinating disease; a drug-induced movement disorder; a disorder of the motor unit; Down's Syndrome in middle age; Senile Dementia of Lewy body type; an effect of chronic alcoholism; Subacute sclerosing panencephalitis; a neurological developmental disease; infantile spinal muscular atrophy; and juvenile spinal muscular atrophy.*

* * * * *